United States Patent [19]
Shah

[11] Patent Number: 6,068,852
[45] Date of Patent: May 30, 2000

[54] POLYMERIC COMPOSITION FOR SEALING AND SHIELDING ANIMAL SKIN

[75] Inventor: Kishore R. Shah, Bridgewater, N.J.

[73] Assignee: Polytherapeutics, Inc., Bridgewater, N.J.

[21] Appl. No.: 08/988,742

[22] Filed: Dec. 11, 1997

Related U.S. Application Data

[63] Continuation-in-part of application No. 08/947,537, Oct. 11, 1997, abandoned.

[51] Int. Cl.⁷ .............................. A61F 5/443; A61F 13/00
[52] U.S. Cl. ........................... 424/443; 424/401; 604/332; 604/336
[58] Field of Search ..................................... 424/443, 401; 604/332, 336; 521/50

[56] References Cited

U.S. PATENT DOCUMENTS

| | | |
|---|---|---|
| 3,980,084 | 9/1976 | Kross . |
| 4,578,065 | 3/1986 | Habib . |
| 5,428,076 | 6/1995 | Roe . |
| 5,494,987 | 2/1996 | Imazato et al. . |

*Primary Examiner*—Thurman K. Page
*Assistant Examiner*—Brian K. Seidleck
*Attorney, Agent, or Firm*—Roberts & Mercanti, LLP

[57] ABSTRACT

A two part, polymerizable, skin sealant or shield which cures in situ to form a custom made, solid, shaped, skin friendly barrier which absorbs aqueous fluids without disintegrating.

20 Claims, No Drawings

POLYMERIC COMPOSITION FOR SEALING AND SHIELDING ANIMAL SKIN

This application is a continuation-in-part of application U.S. Ser. No. 08/947,537, entitled Polymeric Composition for Sealing and Shielding Animal Skin, filed Oct. 11, 1997 now abandoned.

FIELD OF THE INVENTION

This invention pertains to a novel and improved sealant and skin shield which find use in conjunction with appliances for the management of ostomy. More specifically, this invention relates to two-part solventless, paste like polymeric sealing compositions, which after being uniformly mixed and applied at the skin site, easily flow into various contours, folds or crevices of the skin and subsequently undergo in situ gelation and curing via crosslinking reactions to form an adherent, moisture absorbent, non-disintegrating, skin friendly, solid barrier protecting the peristomal skin from the corrosive effects of the stomal effluents. These polymeric sealant compositions may also have other skin protecting applications, such as use with apparatus for management of fecal incontinence and for use around fluid drainage openings like wound or surgical incision sites. The two-part pastes of the present invention may also be used to create a protective barrier to prevent skin damage, e.g. bed sores. It is also within the purview of the present invention to use the skin shield for nonmedical uses, such as beneath a mask, or in any other use where the skin will benefit from a comfortable, moisture absorbing protective layer.

BACKGROUND OF THE INVENTION AND PRIOR ART

Surgical procedures, known as ostomies, are some times necessitated due to inflammatory bowel disease, cancer, or injury. An ostomy creates an artificial opening (stoma) in the abdomen for the elimination of bodily waste. Since the ostomy patients are unable to control the passage of bodily waste material, use is made of an appliance attached to the body to collect this material. Conventional available ostomy appliances consist of a pouch, made up of a barrier plastic material, attached to a hydrocolloid containing synthetic rubber based adhesive gasket capable of adhering to the skin around the stoma. The adhesive gasket is capable of anchoring the appliance to the skin for time periods ranging from one day to as long as 10 days. The adhesive gasket does protect the peristomal skin. However, it is very difficult for the ostomate to cut a hole in the wafer to fit perfectly around the stoma to achieve a fluid proof seal between the stomal opening of the gasket and the stoma. Therefore, some areas of the peristomal skin may remain exposed and become vulnerable to the deleterious effects of the intestinal effluents, which can cause serious irritation, excoriation, and eventual breakdown of the skin contiguous to the stoma. In addition, the fluid leakage may also cause disintegration of the gasket, resulting in breach of its barrier properties and exacerbating the problem of skin protection. Another frequent cause of peristomal skin complications is stomal effluent undermining a skin barrier due to irregularities in stoma placement, stoma shape, retraction or scarring. When peristomal surface unevenness is severe, the appliance gasket may fail to achieve an acceptable seal resulting in undermining of the gasket by the stomal effluent, causing leakage, discomfort and pain.

For these reasons, many ostomates use one of the additional means available in the form of pastes, hydrocolloid powders, karaya seal rings, skin barrier rings, or adhesive strips to augment the sealing function of the gasket. Some of the commercially available paste products include those under trade names Stomahesive™ Paste (ConvaTec, Bristol-Myers Squibb), Proshield Plus (Health Point), Hollihesive Paste (Hollister Incorporated), Coloplast Ostomy Paste (Coloplast Sween Corporation), and Dansac Soft Paste (Incutech Inc.). One of the disadvantages of such pastes is that some of them contain solvents, which are irritating to skin. The other disadvantage is that the pastes are easily subject to disintegration upon fluid absorption. Therefore, their protective effect is not long lasting.

U.S. Pat. No. 4,204,540 describes a composition adapted for use around the stoma and consisting of a homogeneous mixture of a pressure-sensitive adhesive component, mineral oil, and hydrocolloid gums or cohesive strengthening agents or a mixture of hydrocolloid gums and cohesive strengthening agents. A balance of different components in the mixture provides compositions which can be shaped by hand to seal the skin surface between the gasket and the stoma.

U.S. Pat. No. 4,231,369 describes a gel like sealant composition composed of a physical mixture of tackified styrene-olefin-styrene block copolymer having at least one hydrocolloid dispersed therein.

U.S. Pat. No. 4,350,785 describes an ostomy paste formulated as mixtures of water absorbing particulate hydrocolloid gums and organic solvent (e.g. alcohol) solutions of adhesive film forming resins, such as poly(methyl vinyl ether/maleic acid), having increased resistance to urine and intestinal fluids by incorporating a small amount of colloidal silica, preferably fumed silica.

U.S. Pat. No. 4,578,065 describes protective sealing compositions in the form of molded rings or sheets, which comprise gelled mixtures of water absorbing particulate hydrocolloid gum and non-toxic polyhydroxyalcohol, having increased resistance to the drained fluid (e.g. urine or intestinal fluids) by incorporating a small amount of fumed silica or colloidal silica gel.

U.S. Pat. No. 4,477,325 to Osburn decribes sealant or paste composition of hydrocolloids in a network of an elastomeric copolymer of ethylene and vinyl acetate, and polyisobutylene; the mechanical strength and fluid endurance of which is enhanced by crosslinking, produced by irrradiating the mixture.

U.S. Patent No. 4,738,257 to Meyer et al describes a continuous elastomeric phase, formed by cross-linking to form a network, and distinguishes itself by stating that in Sorensen and Osburn, above, that after absorbing enough water, the hydrocolloid loses its wet tack, or ability to adhere to the skin to form a sealant or shield.

U.S. Pat. No. 5,496,296 describes an ostomy appliance having an adhesive gasket, which includes a flexible patch which may be formed of non-woven material and is covered on one side with a first layer of moisture absorbing pressure-sensitive adhesive material surrounding the stomal opening, and a second layer of a soft, easily deformable, extrudable fluid resistant gasket that prevents stomal fluids form contacting the peristomal skin surfaces and the first layer of the adhesive and possibly dissolving that layer and/or disrupting its attachment to skin.

SUMMARY OF THE INVENTION

An object of the present invention is to provide skin friendly, solventless, liquid polymeric formulations for use in conjunction with ostomy appliances for application around the stoma to protect the peristomal skin from the corrosive stomal effluents, as well as for use with apparatus for fecal incontinence, and for use around wound and surgical drainage openings.

Another object of the invention is to provide liquid polymeric materials in two-parts, which upon uniform mixing and application at the skin site easily flows into skin contours, folds and crevices and subsequently undergoes self curing and crosslinking to form soft, flexible, and coherent rubbery mass capable of absorbing aqueous fluids and tightly adhering to skin. An additional object of the invention is to provide a liquid polymeric sealant, which is easy to apply and after crosslinking at the site of application does not disintegrate even after absorption of bodily fluids for as long as the ostomy appliance is in place around the stoma.

It is yet another object of the invention to provide a skin shield which is moisture absorbing, and hence comfortable, and soft and elastomeric, yielding to pressure but returning to its original shape. The shield may be applied at e.g. the elbows, to cushion them and prevent bed sores. In fact the shield may be applied to any area of the skin which may undergo mechanical or other stress. The skin friendly components, and the mild adherence of the shield produce a shield which protects from mechanical damage, does not stress the skin with chemicals, is not difficult to remove, and removes completely, even when wet.

The two-part paste compositions of this invention, formulated to accomplish the aforementioned objectives, are comprised of particulate dispersions of at least one moisture absorbent hydrocolloid polymer, and optionally a non-moisture absorbent filler and fumed or colloidal silica in a liquid polymer having free radical polymerizable ethylenically unsaturated groups at some or all of its chain ends or at branch points along the main chain. Optionally the liquid polymer may contain small amounts of a skin compatible monomer having one or more ethylenically unsaturated groups capable of free radical copolymerization with the reactive liquid polymer. Examples of liquid polymeric materials include, but are not limited to, acrylated or methacrylated urethane prepolymners, epoxy acrylates and methacrylates, epoxidized soybean oil acrylate or methacrylate, polyester acrylates and methacrylates, and polyether acrylates and methacrylates. An essential requirement for the liquid reactive polymeric material is that it be free of low molecular weight monomers, which may be toxic and/or irritating to skin. Optionally the formulation may contain diluents or plasticizers such as poly(ethylene oxide) or poly(propylene oxide).

One of the two-part formulation contains a small amount of a thermally stable polymerization initiator. The second part contains a small amount of an activator for the initiator. The crosslinking reaction of the reactive liquid polymer resulting in its gelation does not commence until the initiator and the activator parts are combined. When predetermined proportions of the two parts of the formulation are homogeneously mixed together the mixture polymerizes and sets to a non-flowing, coherent, soft rubbery mass within a period of say 10 to 60 minutes depending upon the reactivity of the liquid polymer/monomer mixture, and the concentrations of the initiator and the activator. In actual practice, the two parts can be appropriately packaged so that the user can easily dispense the two parts, mix and apply on the peristomal skin. The user does not have to wait for setting of the formulation in order to apply the ostomy appliance on to it. The sealant readily polymerizes under the ostomy gasket. Once the polymerization is complete, the sealant is very stable, and does not disintegrate by the effect of the intestinal effluents or transepidermal water loss because of its covalently crosslinked network structure. The cured sealant can absorb up to 300–400 % of aqueous fluids based on the weight of the dry sealant. Therefore, there is no maceration of the skin it is adhering to. Although the sealant exhibits good adherence to skin, it does not cause any discomfort or pain to the patient when it is removed.

DETAILED DESCRIPTION OF THE PREFERRED EMBODIMENTS

The present invention is directed to a new and improved ostomy paste used to protect exposed skin around stoma and as a filler for skin folds, uneven skin surfaces, and scarring. The skin protecting applications for the improved past e materials of this invention include use with apparatus for fecal incontinence, and wound and surgical drainage sites, and any area that has or may undergo stress of various kinds. The paste is provided as a two-part system. In one preferred embodiment, each part contains primarily a dispersion of at least one moisture absorbing particulate hydrocolloid polymer in a liquid polymer having free radical polymerizable ethylenically unsaturated groups at one or more of its chain ends or at branch sites along the main chain. Optionally, the liquid polymer may contain a plasticizer and a small amount of skin compatible monofunctional or multifunctional ethylenically unsaturated monomer, which is copolymerizable with the liquid polymer. The paste may also contain particulate non moisture absorbent fillers and/or fumed or colloidal silica.

One of the two parts of the paste contains a small amount of a polymerization initiator. The second part of the paste contains small amounts of an activator for the initiator. When predetermined proportions of the two parts of the formulation are homogeneously mixed together, the mixture polymerizes and sets to a non-flowing, coherent, soft rubbery mass within a period of say 10 to 60 minutes depending upon the mix ratio and the concentrations of the initiator and the activator. In actual practice, the two parts can be appropriately packaged so that the user can easily dispense the two parts, mix and apply on the peristomal skin. The user does not have to wait for setting of the formulation in order apply the ostomy appliance on to it. The sealant readily polymerizes under the ostomy gasket.

Components of this invention are carefully selected to obtain the desired balance of handling, flow characteristics, and the cure time of the paste, and moisture absorption, softness, flexibility, and cohesiveness of the cured material even after its equilibrium hydration. The paste must be viscous enough not to be runny at the site of application. At the same time, it should have some flow or spreadability to fill into uneven contours of the skin.

The compositions of this invention are very distinct from those of the prior art, which are basically dispersions or gels of hydrocolloids and rubbery or film forming polymers in liquids such as mineral oil, solvent, or polyhydroxy compounds. On the other hand, the compositions of this invention are dispersions of hydrocolloids in viscous reactive polymeric liquids. In situ chemical reactivity (crosslinking) is a unique feature of these compositions, and is a major point of differentiation from the prior art. Easy flow and leveling of the paste into and over the peristomal skin contours followed by "chemical setting" to a solid rubbery mass permits an ostomate to form a skin protecting barrier "customized" to each individual ostomate.

An essential requirement of the liquid polymer is that it be free of low molecular weight monomers, which may be toxic and/or irritating to skin. Another requirement is that after curing, the resultant material should have a glass transition temperature (Tg) of less than 25° C., so that it is soft and flexible. The liquid polymers which crosslink to materials having a Tg of greater than 25° C., can be used if plasticized with a suitable plasticizer. Functionality of the liquid polymer should be greater than 1 in order to attain a crosslinked network. For the purpose of this invention the functionality is defined as the average number of polymerizable ethylenically unsaturated groups per each polymer chain. Although there is no absolute limit of the viscosity of the liquid polymer, it should be sufficiently fluid for handling convenience. For this purpose reactive liquid polymers should have a viscosity of less than 150,000 cps, and preferably less than 100,000 cps. Higher viscosity materials need to be diluted with suitable plasticizers for use in this invention. Different kinds of liquid polymers that can be used in this invention include, but are not limited to, acrylated or methacrylated urethane prepolymers, epoxy acrylates and methacrylates, epoxidized soybean oil acrylate or methacrylate, polyester acrylates and methacrylates, and polyether acrylates and methacrylates. Specific examples of the liquid polymers, commercially available from Sartomer Company and UCB Chemical Corporation are described in Table 1. The amounts of the liquid polymers present may vary from 30 to 75 %, and preferably from 45 to 70 % by weight based on the total weight of the paste.

The use of a plasticizer in the paste helps to reduce the viscosity of the paste, and at the same time makes the cured paste soft and more flexible. Any of the commercially available skin compatible plasticizers can be used in the paste as long as it is miscible with the liquid polymer at the concentrations used. Examples of suitable plasticizers include, but are not limited to, polyethylene glycol (mol. wt. 400–600), polypropylene glycol, triethyl citrate, and triacetin. The relative amounts of the plasticizer in the paste may vary from 0 to 26%, and preferably from 0 to 10% by weight based on the total weight of the paste.

Free radical polymerization initiator for use in this invention are selected to possess a balance of the following characteristics. They should be non irritating or non sensitizing to skin at the concentrations used in the paste. Its reactivity in combination with an activator should be sufficient to cure the paste at room temperature within a period of 60 minutes. At the same time it must be thermally stable by itself at normal storage temperatures so that premature gelation or curing of the paste does not occur during storage. The combination of initiator and activator forms a redox polymerization system. Therefore, the initiator and the activator are provided in two separate paste parts, which are combined just prior to use. These redox systems are generally composed of a peroxy compound (initiator) and a reducing agent (activator). Many of the redox systems used in the chemically setting acrylic dental restorative compo-

TABLE 1

SUITABLE REACTIVE LIQUID POLYMERS

| LIQUID POLYMER | MANUFACTURER | CHEMICAL CLASS | FUNCTIONALITY | Tg ° C. | VISCOSITY cps(° C.) |
| --- | --- | --- | --- | --- | --- |
| CN 934 | Sartomer | Aliphatic Urethane Acrylate | 2 | −30 | 25,000(40) |
| CN 975 | Sartomer | Aromatic Urethane Acrylate | 6 | 88 | 450(60) |
| CN 104 | Sartomer | Epoxy Acrylate | 2 | −5 | 19,000(49) |
| Ebecryl 230 | UCB | Aliphatic Urethane Acrylate | 2 | −55 | 40,000(25) |
| Ebecryl 270 | UCB | Aliphatic Urethane Acrylate | 2 | −27 | 2,700(60) |
| Ebecryl 6700 | UCB | Aromatic Urethane Acrylate | 2.3 | −21 | 6,000(65) |
| Ebecryl 1657 | UCB | Polyester Acrylate | 4 | 33 | 120,000(25) |
| Ebecryl 860 | UCB | Epoxidized Soya Oil Acrylate | 3 | 13 | 25,000(25) |

Many of the known acrylate and related low molecular weight monomers are generally toxic and/or irritating to the skin. However, some monomers, especially those based on polyalkylene glycols, have low skin irritation. Small amounts of such monomers may be used in the paste compositions for copolymerization with the liquid polymer. The copolymerizable monomers function to increase reactivity of the liquid polymers, reduce viscosity, and modify crosslinking functionality of the paste composition. Examples of such monomers, commercially available from Sartomer Company, Inc., include ethoxylated trimethylolpropane triacrylate (mol. wt. 1,176), propoxylated trimethylolpropane triacrylate (mol. wt. 645), dipentaerythritol pentaacrylate (mol. wt. 525), di-trimethylolpropane tetraacrylate (mol. wt. 482), ethoxylated bisphenol A diacrylate (mol. wt. 424), polyethylene glycol 400 diacrylate (mol. wt. 508), and polypropylene glycol monomethacrylate (mol. wt. 405). In general, monomers having a molecular weight greater than 400 are preferred. Another particularly useful copolymerizable material is allylglycidyl ether alcohol resin (mol. wt. 1200), commercially available from Monsanto Company under the trade name Santolink XI-100. The amounts of the copolymerizable monomer in the paste may vary from 0 to 20%, preferably from 0 to 10%, and most preferably from 0 to 5% by weight based on the total weight of the paste.

sitions are suitable for use in this invention. Examples of such redox systems are described in "Concise Encyclopedia of Medical & Dental Materials", D. Williams, ed., Pergamon Press, 1990, U.S. Pat. No. 5,151,479, and U.S. Pat. No. 3,991,008. Benzoyl peroxide is a common initiator for use in the paste. Suitable activators for benzoyl peroxide include N,N-dihydroxyethyl-p-toluidine, sodium p-toluene sulfinate, and N,N-diethanol-3,5-di-t-butylaniline. Another group of suitable initiators is hydroperoxides, which include p-menthane hydroperoxide, cumene hydroperoxide, t-butyl hydroperoxide, and diisopropylbenzene hydroperoxide. Suitable activators for use with hydroperoxides include various thiourea compounds described in U.S. Pat. No. 3,991,008. A particularly useful activator is 1-allyl 2-thiourea. It is important to keep the concentrations of the redox system components in the paste as low as possible. At higher concentrations, particularly with hydroperoxides, skin irritation or sensitization may occur. The relative amounts of both the initiator and the activator in the paste (after the two parts are combined) may vary from 0.5 to 2.0%, and preferably from 0.5 to 1.2% by weight of each component based on the total weight of the two combined paste parts.

The dispersed components of the paste give it a "body", that is increased resistance to deformation or flow under gravity, and shear thinning characteristics to reduce stringiness (elasticity) of the liquid polymer. In general, for optimum dispersion stability, the particle size of the dispersed components should be less than 100 microns and preferably less than 50 microns.

The hydrocolloids provide moisture absorption characteristics to remove the transepidermal water loss from the surface of the skin so that the skin does not get macerated and eventually damaged. Examples of suitable hydrocolloids include sodium caboxymethyl cellulose, microcrystalline cellulose, hydroxypropyl methyl cellulose, crosslinked carboxymethyl cellulose, starch-acrylonitrile graft copolymer, crosslinked dextran, guar gum, locust bean gum, karaya gum, pectin, gelatin, poly(vinyl alcohol), poly(vinyl pyrrolidone), high molecular weight poly(ethylene oxide), etc. and mixtures thereof. Various hydrocolloids described in U.S. Pat. Nos. 4,350,785, 4,204,540, and 4,231,369 may also be used in this invention, and are incorporated herein by reference. The amounts of the hydrocolloids used may vary from 10 to 30%, and preferably from 10 to 20% by weight based on the total weight of the paste.

Optionally, non absorbent particulate materials, having a particle size less than 100 microns and preferably less than 50 microns, may be used in the paste compositions. Fillers perform a similar function as the hydrocolloids but without increasing the moisture absorption characteristics of the cured paste. Examples of suitable non absorbent fillers include zinc oxide and talc. The amounts of the fillers used in the paste may vary from 0 to 20% by weight based on the total weight of the paste.

Another optional ingredient for the paste formulations is fumed or colloidal silica, which functions as a thixotropic agent (shear thinning) and a thickener even when used in very small amounts. Fumed silica also aids in the prevention of separation, which can result in settling or sedimentation, of other particulate ingredients of the paste. Fumed silica, such as Cab-O-Sil M-5 P (Cabot Corporation), is particularly suitable for use in this invention. The amounts of the silica used may vary from 0 to 6% and preferably from 0 to 4% by weight based on the total weight of the paste.

The method of preparation of each of the two paste parts of the formulation involves mixing the different components in a vessel employing a mechanical agitator capable of mixing dough like materials. Preferably, the mixing is done in a vacuum mixer to avoid the formation of air bubbles in the paste. The liquid components, namely the liquid polymer, the monomer and the plasticizer, and the initiator or the activator are mixed first followed by silica if used in the formulation. The other particulate components are then added in small increments and mixed thoroughly to produce a smooth paste without any grittiness or lumps.

EXAMPLES

Example 1

Compositions for the initiator (cumene hydroperoxide) containing paste (Part A) and the activator (1-allyl 2-thiourea) containing paste (Part B) are described in Table 2. Preparation of the pastes was done by the general method described earlier. 1-Allyl 2-thiourea was added to the liquid components as its solution in poly(ethylene glycol). Both Part A and Part B were obtained as a smooth paste. Approximately 5 grams each of Part A and Part B were mixed thoroughly by a spatula in an aluminum weighing dish and allowed to stand at room temperature. Within a period of 30 minutes a flexible, cured solid mass was obtained.

TABLE 2

OSTOMY PASTE COMPOSITION

| | COMPOSITION, WT % | |
|---|---|---|
| COMPONENT | PART A | PART B |
| Urethane Acrylate CN 934 (Sartomer) | 60 | 60 |
| Santolink XI-100 (Monsanto) | 3 | 3 |
| Polyethylene Glycol 400 (Aldrich) | 6 | 6 |
| Modified Cellulose Gum* | 14.2 | 14.2 |
| Zinc Oxide (Aldrich) | 14.2 | 14.2 |
| Cab-O-Sil (Cabot) | 1.4 | 1.4 |
| Cumene Hydroperoxide (Aldrich) | 1.2 | — |
| 1-Allyl 2-Thiourea (Aldrich)- | — | 1.2 |

*Accelerate ™ DS-812, FMC Corp

In a separate test of the formulation of this example, equal proportions (~5 grams) of the Parts A and B were mixed and then pressed into a sheet between two pieces of aluminum foil. After allowing the mixture to stand for 30 minutes, the cured sample in the form of a soft, flexible solid sheet was separated from the foil. Water Uptake characteristic of this sheet was measured by placing a 1 square inch specimen over a sponge soaked and immersed in normal saline, and weighing the sample at different time intervals (Time, t). During the entire experiment the vessel containing the sponge and the sample was covered with a 4-mil thick film of polyethylene and sealed. Percent water uptake was calculated as follows:

$$\% \text{ Water Uptake} = \frac{\text{Wt. of Sample at Time } t - \text{Initial Wt. of the Sample}}{\text{Initial Wt. of the Sample}} \times 100$$

The water uptake at 3.5, 29, and 72 hour time points was 73, 196, and 312%, respectively. After 196% water uptake the sample was swollen and it still exhibited good integrity and strength. After 312% water uptake the sample was even more swollen, but it still had good integrity and did not disintegrate although it had become some what weaker. When the sample was further allowed to equilibrate in water over the sponge for a period of additional 7 days, there was no further change in the water uptake or its integrity. In comparison, the water uptake of a commercially available ostomy gasket (Stomahesive™, ConvaTec) at the 3.5 hour time point was 145%. After 24 hours, the hydrocolloid adhesive of Stomahesive™ had partially liquified and partially disintegrated.

Example 2

Paste samples, 3.4 grams each, of the Part A and Part B of Example 1 were thoroughly mixed in an aluminum weighing dish. Approximately 2 grams of the mixture was spread around the stomal opening of Stomahesive™ ostomy gasket and positioned tightly against uneven skin surface of a human subject. The remaining material in the weighing dish solidified within 30 minutes. After a period of 45 minutes from the initial application, the ostomy gasket was removed to examine the nature of the paste cured in vivo. The paste mixture had cured to a solid, soft, and flexible mass tightly adhering to and conforming to the uneven skin surface. The cured solid was then peeled away from the skin without any discomfort. There was no evidence of any skin irritation.

Examples 3–6

The compositions for the paste formulations of examples 3–6 are shown in Table 3. As shown in Table 4, all the formulations, when the Parts A and B were prepared, mixed in equal proportions, and cured in a manner analogous to that that described in Example 1, solidified within a period of 26 minutes and had a 24 hour water uptake values ranging from 99 to 237%.

TABLE 3

OSTOMY PASTE COMPOSITIONS

COMPOSITION, WT. %

| EXAMPLE NO. | 3 | | 4 | | 5 | | 6 | |
|---|---|---|---|---|---|---|---|---|
| COMPONENT | A | B | A | B | A | B | A | B |
| Urethane Acrylate CN 934 | 60 | 60 | — | — | — | — | — | — |
| Urethane Acrylate CN 965 | — | — | 60 | 60 | 60 | 60 | — | — |
| Urethane Acrylate CN 981 | — | — | — | — | — | — | 60 | 60 |
| Dipentaerythritol Pentaacrylate | 4.5 | 4.5 | 4.5 | 4,5 | — | — | — | — |
| Santolink XI-100 | — | — | — | — | 4.5 | 4.5 | 4.5 | 4.5 |
| Polyethylene Glycol 400 | 6.5 | 6.5 | 6.5 | 6.5 | 6.5 | 6.5 | 6.5 | 6.5 |
| Modified Cellulose Gum | 20 | 20 | 20 | 20 | 20 | 20 | 20 | 20 |
| Zinc Oxide | 7 | 7 | 7 | 7 | 7 | 7 | 7 | 7 |
| Cumene Hydroperoxide | 2 | — | 2 | — | 2 | — | 2 | — |
| 1-Allyl 2-Thiourea | — | 2 | — | 2 | — | 2 | — | 2 |

TABLE 4

KEY PROPERTIES OF OSTOMY PASTE COMPOSITIONS

| EXAMPLE NO. | CURE TIME, MINUTES | 24 HR WATER UPTAKE, % |
|---|---|---|
| 3 | 22 | 237 |
| 4 | 16 | 99 |
| 5 | 23 | 143 |
| 6 | 26 | 202 |

In practicing the method of the present invention, parts one and two are mixed, just prior to making the seal or shield, to form a paste composition. The paste composition is then applied to the skin where desired, and additional appliances or devices applied as necessary, on or about the position of the paste. If desired the paste may be applied to the appliance or device, and thereby placed in contact with the skin.

To assist e.g. the ostomate in using the paste compositions of the present invention, premeasured amounts of part one and part two may be placed in an individually sealed pouches, yielding the proper proportion of part one to part two upon mixing. The individually sealed pouches may be mounted to a common backing or mounting to ensure that the appropriate components are mixed together. A mixing pouch may be provided, preferably connected to the individually sealed pouches by barriers which may be easily broken to permit the admixture of parts one and two. In an alternative construction, the individually sealed pouches may be separated by one barrier, which when broken, creates a mixing pouch of the combined volume of the individual pouches.

Alternatively, the paste composition may be metered out of a two port container for dispensing the proper ratio of parts one and two of said paste composition. Side by side dispensing is well known, an example being the dispenser for Mentadent toothpaste. The concentrations of parts one and two need to be coordinated with the relative volumes the container is able to dispense. Containers for dispensing two solutions may be adjusted to vary the ratio of the two solutions. Additional tubes, or other volumes, of parts one and two may be provided, with means for attaching them to the container for their dispensing, and optionally, with attachment means which correlate the solutions to the appropriate port for dispensing of the proper volumes and/or ratios.

We claim:

1. A two-part, protective sealing composition in the form of a liquid paste, for use in conjunction with ostomy appliances, incontinence apparatus, and for use around surgical or wound drainage sites, said two part protective sealing composition comprising, a first part, comprising a free radical polymerization initiator, and, a second part, comprising an activator for the initiator, and the first, second or both parts of said paste composition further comprising an ethylenically unsaturated liquid polymer capable of free radical polymerization by means of the initiator, the total weight of said liquid polymer comprising from about 30%-about 75% by weight of said liquid paste sealing composition, and at least one hydrocolloid polymer dispersed therein, the total weight of said hydrocolloid polymers comprising from 10%-about 40% by weigh of said liquid paste sealing composition, said first part and said second part, upon mixing, forming a liquid paste which cures in situ, to form a solid, shaped, skin friendly barrier, which absorbs aqueous fluids without disintegration.

2. The two-part paste composition of claim 1, wherein said first, second, or both parts of said paste composition further comprise a non-moisture absorbent filler uniformly dispersed therein, the total weight of said filler in said paste composition comprising 0%-about 20% by weight of said paste composition.

3. The two-part paste composition of claim 1, wherein the first, second, or both parts of said paste composition further comprise a skin compatible monofunctional or multifunctional ethylenically unsaturated monomer of molecular weight>400 uniformly dissolved in, and copolymerizable with, said liquid polymer, the total weight of said monomer comprising 0%-about 20% by weight of said paste composition.

4. The two-part paste composition of claim 1, wherein the first, second, or both parts of said paste composition further comprise a plasticizer uniformly dissolved therein, comprising 0%-about 26% by weight of said paste composition.

5. A two-part paste composition, as in claim 4, wherein the free radical polymerization initiator comprises from about 0.5%-about 2% by weight of said paste composition, and the activator for the initiator comprises from about 0.5%-about 2% by weight of said paste composition.

6. The two-part paste composition of claim 1, wherein the ethylenically unsaturated liquid polymer is selected from the group consisting of acrylated or methacrylated urethane prepolymers, epoxy acrylates and methacrylates, epoxidized soybean oil acrylate or methacrylate, polyester acrylates and methacrylates, and polyether acrylates and methacrylates.

7. The two-part paste composition of claim 1 wherein the hydrocolloid polymer or polymers are selected from the group consisting of sodium carboxymethyl cellulose, microcrystalline cellulose, hydroxypropyl methyl cellulose, cross-linked carboxymethyl cellulose, starch acrylonitrile graft copolymer, cross-linked dextran, guar gum, locust bean gum, karaya gum, pectin, gelatin, poly(vinyl alcohol),poly(vinyl pyrrolidone), high molecular weight poly(ethylene oxide), and mixtures thereof.

8. The two-part paste composition of claim 1, wherein the initiator is selected from the group consisting of benzoyl peroxide, hydroperoxides, including p-methane hydroperoxide, cumene hydroperoxide, t-butyl hydroperoxide, and diisopropylbenzene hydroperoxide.

9. The two-part paste composition of claim 1, wherein the initiator is benzoyl peroxide, and the activator is selected from the group consisting of N,N-dihydroxyethyl-p-toluidine, sodium p-toluene sulfinate, and N,N-diethanol-3,5-di-t-butylaniline.

10. The two-part paste composition of claim 8, wherein the initiator is a hydroperoxide, and the activator is 1-allyl 2-thiourea.

11. The two-part paste composition of claim 4, wherein the plasticizer is selected from the group consisting of polyethylene glycol, molecular weight 400–600, polypropylene glycol, triethyl citrate, and triacetin.

12. The two-part paste composition of claim 3 wherein the monomer is selected from the group consisting of ethoxylated trimethylolpropane triacrylate, molecular weight 1,176, propoxylatedtrimethylolpropane triacrylate, molecular weight 645, dipentaerythritol pentaacrylate, molecular weight 525, di-trimethylolpropane tetraacrylate, molecular weight 482, ethoxylated bisphenol A diacrylate, molecular weight 424, polyethylene glycol, molecular weight 400, diacrylate, molecular weight 508, polypropylene glycol, monomethacrylate, molecular weight 405, and allylglycidyl ether alcohol resin, molecular weight 1,200.

13. The two-part paste composition of claim 2 wherein the non moisture absorbing filler is selected from the group consisting of zinc oxide and talc.

14. The two-part protective sealing composition of claim 1, cross-linked to form a moisture absorbing, comfortable, soft, elastomeric skin shield.

15. A single use packaging for mixing the two-part paste composition of claim 1, comprising flexible pouches containing said first and second parts, respectively, of said composition, and a mixing pouch, said pouches being separated by barriers sufficient to prevent premature admixture of said parts of the paste composition.

16. A package for shipping and for mixing the two-part paste composition of claim 1, comprising a dual compartment flexible plastic pouch, wherein the first part and the second part of said composition are contained in the two respective sealed compartments separated by a breakable plastic seal, which selectively breaks upon exerting slight pressure on one of the compartments but prevents premature admixture of the parts of the composition.

17. A container for dispensing the two-part paste composition of claim 1, said container being preloaded, or pre-engineered to receive, a specifically compounded first part or second part, said container dispensing said composition in the necessary ratios of first part to second part to form the desired paste composition.

18. A method for making a custom made, skin friendly, protective, aqueous fluid absorbing skin seal or shield using the two part paste composition of claim 1, comprising the steps of, mixing parts one and two to form a paste, applying the paste to the area of the skin where a seal or shield is desired, in sufficient quantity to allow the paste to flow into the contours, folds, and crevices of the skin, and therein undergo self curing to form a soft, flexible and coherent rubbery mass, tightly adhering to the skin.

19. A method for making a custom made, skin friendly, protective, aqueous fluid absorbing skin seal or shield using the two part paste composition of claim 1, comprising the steps of, mixing parts one and two to form a paste, applying to an appliance or device to be attached to the skin, a sufficient quantity of the paste to allow the paste to flow into the contours, folds, and crevices of the skin when applied, and, applying the apparatus or device to the skin within a short period of time of mixing parts one and two, whereby the paste undergoes self curing to form a soft, flexible and coherent rubbery mass, tightly adhering to the skin.

20. The two part paste composition of claim 1, further comprising fumed or colloidal silica uniformly dispersed therein.

* * * * *